United States Patent [19]

Kozima et al.

[11] Patent Number: 5,221,753
[45] Date of Patent: Jun. 22, 1993

[54] PREPARATION OF 1-(4-TETRAHYDROPYRANYL)- OR 1-(4-TETRAHYDROTHIOPYRANYL)PROP-1-EN-3-ONES

[75] Inventors: Shigeru Kozima, Niigata; Masami Hatano, Kanagawa, both of Japan

[73] Assignee: BASF Aktiengesellschaft, Ludwigshafen, Fed. Rep. of Germany

[21] Appl. No.: 547,184

[22] Filed: Jul. 3, 1990

[30] Foreign Application Priority Data

Jul. 4, 1989 [JP] Japan .................... 1-172424

[51] Int. Cl.$^5$ .................... C07D 335/02; C07D 309/06
[52] U.S. Cl. ........................ 549/13; 549/427
[58] Field of Search ................... 549/427, 13

[56] References Cited

U.S. PATENT DOCUMENTS

| | | | |
|---|---|---|---|
| 4,292,244 | 9/1981 | Hoffmann et al. | 549/427 |
| 4,548,932 | 10/1985 | Sugihara | 514/211 |
| 4,591,458 | 5/1986 | Sugihara et al. | 540/491 |
| 4,920,232 | 4/1990 | Goetz et al. | 549/13 |

FOREIGN PATENT DOCUMENTS

| | | |
|---|---|---|
| 0156455 | 10/1985 | European Pat. Off. . |
| 0298380 | 1/1990 | European Pat. Off. . |
| 0352456 | 1/1990 | European Pat. Off. . |
| 7608720 | 2/1977 | Netherlands ............ 549/427 |

OTHER PUBLICATIONS

H. Sugihara et al., *Chemical Abstracts* 104: 129935d, "1,5-Benzothiazepines," p. 706 (1986) and CAS report. Takeda, *Chemical Abstracts* 104: 50900e, "Antihypertensive benzoxazepinones," p. 524 (1986) and CAS report.

*Primary Examiner*—Allen J. Robinson
*Assistant Examiner*—Mark W. Russell
*Attorney, Agent, or Firm*—Keil & Weinkauf

[57] ABSTRACT

A process for the preparation of 1-(4-tetrahydropyranyl)- or 1-(4-tetrahydrothiopyranyl)prop-1-en-3-ones of the general formula I

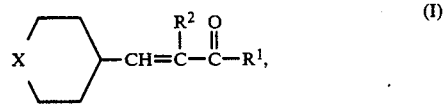

where
$R^1$ is hydrogen, $C_1$- to $C_{10}$-alkyl, $C_1$- to $C_{10}$-alkoxy or aryloxy,
$R^2$ is hydrogen, $C_1$- to $C_4$-alkyl, or aryl which is unsubstituted or substituted by $C_1$- to $C_4$-alkyl and/or halogen, and
X is oxygen or sulfur,
by reacting 1-aminoprop-1-en-3-ones of the general formula II

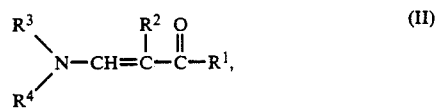

where
$R^1$ and $R^2$ are as defined above, and
$R^3$ and $R^4$, independently of one another, are hydrogen, $C_1$- to $C_4$-alkyl, aryl or together are a $C_2$- to $C_7$-alkylene chain,
with a 4-tetrahydropyranyl- or 4-tetrahydrothiopyranylmagnesium halide of the general formula III

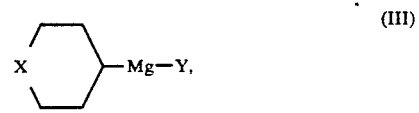

where X is as defined above and Y is halogen, at from $-20°$ to $100°$ C.,
and novel 1-(4-tetrahydropyranyl)- or 1-(4-tetrahydrothiopyranyl)prop-1-en-3-ones are described.

2 Claims, No Drawings

PREPARATION OF 1-(4-TETRAHYDROPYRANYL)- OR 1-(4-TETRAHYDROTHIOPYRANYL)PROP-1-EN-3-ONES

The present invention relates to a novel process for the preparation of 1-(4-tetrahydropyranyl)- or 1-(4-tetrahydrothiopyranyl)prop-1-en-3-ones and to novel 1-(4-tetrahydropyranyl)-or 1-(4-tetrahydrothiopyranyl)-prop-1-en-3-ones.

DE-A-3,437,238 and DE-A-3,536,117 disclose the preparation of $\alpha,\beta$-unsaturated carbonyl compounds by the condensation reaction of aldehydes with ketones, specifically acetone, with catalysis by bases, to give $\alpha,\beta$- and $\beta,\gamma$-isomer mixtures, which can only be separated using considerable effort.

It is therefore an object of the present invention to overcome the abovementioned disadvantages.

We have found that this object is achieved by a novel and improved process for the preparation of 1-(4-tetrahydropyranyl)-or 1-(4-tetrahydrothiopyranyl)prop-1-en-3-ones of the general formula I

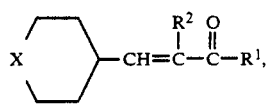   (I)

where
$R^1$ is hydrogen, $C_1$- to $C_{10}$-alkyl, $C_1$- to $C_{10}$-alkoxy or aryloxy,
$R^2$ is hydrogen, $C_1$- to $C_4$-alkyl, or aryl which is unsubstituted or substituted by $C_1$- to $C_4$-alkyl and/or halogen, and
X is oxygen or sulfur,
which comprises reacting 1-aminoprop-1-en-3-ones of the general formula II

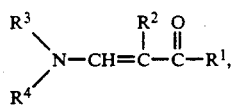   (II)

where
$R^1$ and $R^2$ are as defined above, and
$R^3$ and $R^4$, independently of one another, are hydrogen, $C_1$-to $C_4$-alkyl, aryl or together are a $C_2$- to $C_7$-alkylene chain,
with a 4-tetrahydropyranyl- or 4-tetrahydrothiopyranylmagnesium halide of the general formula III

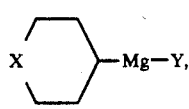   (III)

where X is as defined above and Y is halogen, at from $-20°$ to $100°$ C.,
and by novel 1-(4-tetrahydropyranyl)- or 1-(4-tetrahydrothiopyranyl)prop-1-en-3-ones of the general formula I′

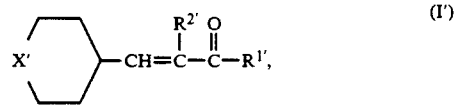   (I′)

where the substituents have the following meanings:
$R^{1'}$ is hydrogen, $C_1$- to $C_{10}$-alkyl, $C_1$- to $C_{10}$-alkoxy or aryloxy,
$R^{2'}$ is hydrogen, $C_1$- to $C_4$-alkyl, or aryl which is unsubstituted or substituted by $C_1$- to $C_4$-alkyl and/or halogen, and
$X'$ is oxygen or sulfur.

The process according to the invention can be carried out as follows:

A 1-aminoprop-1-en-3-one of the formula II is added to a solution or suspension or slurry of a 4-tetrahydropyranyl-or 4-tetrahydrothiopyranylmagnesium halide of the formula III at from $-20°$ to $100°$ C., preferably at from $-10°$ to $50°$ C., particularly preferably at from $0°$ to $20°$ C.

The III:II molar ratio is from 0.8:1 to 20:1, preferably from 1:1 to 5:1, particularly preferably from 1:1 to 1.2:1.

Suitable solvents are all solvents which are customary for Grignard reactions, for example dipolar, aprotic organic solvents, e.g. ethers, such as diethyl ether, methyl tert.-butyl ether, tetrahydrofuran, dioxane and dimethyl glycol ether; or amines, such as triethylamine, or apolar, aprotic organic solvents, e.g. aliphatic hydrocarbons, such as cyclohexane, or aromatic hydrocarbons, such as benzene or toluene, as a mixture with dipolar, aprotic solvents. Preference is given to acyclic and cyclic ethers, such as diethyl ether, methyl tert.-butyl ether, tetrahydrofuran, dioxane and dimethyl glycol ether. Particular preference is given to cyclic ethers, such as tetrahydrofuran and dioxane.

Suitable tetrahydropyranyl- and tetrahydrothiopyranylmagnesium halides of the formula III are the fluorides, chlorides, bromides and iodides, preferably the chlorides and bromides.

The tetrahydropyranyl- and tetrahydrothiopyranylmagnesium halides of the formula III can be prepared in a conventional manner by reacting tetrahydropyranyl halides or tetrahydrothiopyranyl halides with magnesium in one of the solvents which is customary for Grignard reactions.

The tetrahydropyranyl halides and tetrahydrothiopyranyl halides are readily accessible from tetrahydropyran-4-ol and tetrahydrothiopyran-4-ol respectively.

The substituents $R^1$ and $R^2$ in the compounds I and II, the cyclic member X in the compound I, and $R^3$ and $R^4$ in the compound II have the following meanings:

$R^1$
hydrogen,
$C_1$- to $C_{10}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec.-butyl and tert.-butyl,
$C_1$- to $C_{10}$-alkoxy, preferably $C_1$- to $C_8$-alkoxy, particularly preferably $C_1$- to $C_4$-alkoxy, such as methoxy, ethoxy, n-propoxy, isopropoxy, n-butoxy, isobutoxy, sec.-butoxy and tert.-butoxy,
aryloxy, preferably phenoxy, $R^2$
hydrogen,
$C_1$- to $C_{10}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec.-butyl and tert.-butyl, aryl, such as phenyl, 1-naphthyl and 2-naphthyl, preferably phenyl, aryl which is monosubstituted to trisubstituted by $C_1$- to $C_4$-alkyl, preferably phenyl which is monosubstituted to trisubstituted by $C_1$- to $C_4$-alkyl, such as 2-methylphenyl, 4-methylphenyl, 2,4-dimethylphenyl and 2-methyl-4-isopropylphenyl, aryl which is monosubstituted to trisubstituted by halogen, preferably phenyl which is monosubstituted to trisubstituted by halogen, such as 2-chlorophenyl, 2-fluorophenyl, 3-bromophenyl, 3-chlorophenyl, 3-bromophenyl, 3-fluorophenyl, 4-chlorophenyl, 4-bromophenyl, 4-fluorophenyl, 2,4-dichlorophenyl and 2-chloro-4-bromophenyl, aryl which is monosubstituted to trisubstituted by $C_1$- to $C_4$-alkyl and halogen, preferably phenyl which is monosubstituted to trisubstituted by $C_1$- to $C_4$-alkyl and halogen, such as 2-chloro-4-methylphenyl, 4-chloro-2-methylphenyl, 4-chloro-2-isopropylphenyl and 2-fluoro-4-methylphenyl,

X oxygen,
sulfur, $R^3$ and $R^4$ independently of one another, hydrogen, $C_1$- to $C_4$-alkyl, such as methyl, ethyl, n-propyl, isopropyl, n-butyl, isobutyl, sec.-butyl and tert.-butyl, preferably methyl and ethyl, aryl, such as phenyl, 1-naphthyl and 2-naphthyl, preferably phenyl, or together a $C_2$- to $C_7$-alkylene chain, such as $(CH_2)_2$, $(CH_2)_3$, $(CH_2)_4$, $(CH_2)_5$, $(CH_2)_6$ and $(CH_2)_7$, preferably $(CH_2)_4$ and $(CH_2)_5$.

In the compounds I' according to the invention, the substituents $R^{1'}$, $R^{2'}$ and the cyclic member X' have the following meanings:

$R^{1'}$ hydrogen, $C_1$- to $C_{10}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec.-butyl and tert.-butyl, $C_1$- to $C_{10}$-alkoxy, preferably $C_1$- to $C_8$-alkoxy, particularly preferably $C_1$- to $C_4$-alkoxy, such as methoxy, ethoxy, n-propoxy, isopropoxy, n-butoxy, isobutoxy, sec.-butoxy and tert.-butoxy, aryloxy, preferably phenoxy, $R^{2'}$ hydrogen, $C_1$- to $C_{10}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec.-butyl and tert.-butyl, aryl, such as phenyl, 1-naphthyl and 2-naphthyl, preferably phenyl, aryl which is monosubstituted to trisubstituted by $C_1$- to $C_4$-alkyl, preferably phenyl which is monosubstituted to trisubstituted by $C_1$- to $C_4$-alkyl, such as 2-methylphenyl, 4-methylphenyl, 2,4-dimethylphenyl and 2-methyl-4-isopropylphenyl, aryl which is monosubstituted to trisubstituted by halogen, preferably phenyl which is monosubstituted to trisubstituted by halogen, such as 2-chlorophenyl, 2-fluorophenyl, 3-bromophenyl, 3-chlorophenyl, 3-bromophenyl, 3-fluorophenyl, 4-chlorophenyl, 4-bromophenyl, 4-fluorophenyl, 2,4-dichlorophenyl and 2-chloro-4-bromophenyl, aryl which is monosubstituted to trisubstituted by $C_1$- to $C_4$-alkyl and halogen, preferably phenyl which is monosubstituted to trisubstituted by $C_1$- to $C_4$-alkyl and halogen, such as 2-chloro-4-methylphenyl, 2-methyl-4-chlorophenyl, 4-chloro-2-isopropylphenyl and 2-fluoro-4-methylphenyl,

X' oxygen,
sulfur,

Specific examples of the novel compounds I' are the following:

1-(4-tetrahydropyranyl)prop-1-en-3-one
1-(4-tetrahydropyranyl)but-1-en-3-one
1-(4-tetrahydropyranyl)pent-1-en-3-one
1-(4-tetrahydropyranyl)hex-1-en-3-one
1-(4-tetrahydropyranyl)hept-1-en-3-one
1-(4-tetrahydropyranyl)oct-1-en-3-one
1-(4-tetrahydropyranyl)non-1-en-3-one
1-(4-tetrahydropyranyl)dec-1-en-3-one methyl 1-(4-tetrahydropyranyl)eth-1-ene-2-carboxylate
ethyl 1-(4-tetrahydropyranyl)eth-1-ene-2-carboxylate
n-propyl 1-(4-tetrahydropyranyl)eth-1-ene-2-carboxylate
isopropyl 1-(4-tetrahydropyranyl)eth-1-ene-2-carboxylate
n-butyl 1-(4-tetrahydropyranyl)eth-1-ene-2-carboxylate
isobutyl 1-(4-tetrahydropyranyl)eth-1-ene-2-carboxylate
sec.-butyl 1-(4-tetrahydropyranyl)eth-1-ene-2-carboxylate
tert.-butyl 1-(4-tetrahydropyranyl)eth-1-ene-2-carboxylate
tert.-phenyl 1-(4-tetrahydropyranyl)eth-1-ene-2-carboxylate 1-(4-tetrahydrothiopyranyl)prop-1-en-3-one
1-(4-tetrahydrothiopyranyl)but-1-en-3-one
1-(4-tetrahydrothiopyranyl)pent-1-en-3-one
1-(4-tetrahydrothiopyranyl)hex-1-en-3-one
1-(4-tetrahydrothiopyranyl)hept-1-en-3-one
1-(4-tetrahydrothiopyranyl)oct-1-en-3-one
1-(4-tetrahydrothiopyranyl)non-1-en-3-one
1-(4-tetrahydrothiopyranyl)dec-1-en-3-one methyl 1-(4-tetrahydrothiopyranyl)eth-1-ene-2-carboxylate
ethyl 1-(4-tetrahydrothiopyranyl)eth-1-ene-2-carboxylate
n-propyl 1-(4-tetrahydrothiopyranyl)eth-1-ene-2-carboxylate
isopropyl 1-(4-tetrahydrothiopyranyl)eth-1-ene-2-carboxylate
n-butyl 1-(4-tetrahydrothiopyranyl)eth-1-ene-2-carboxylate
isobutyl 1-(4-tetrahydrothiopyranyl)eth-1-ene-2-carboxylate
sec.-butyl 1-(4-tetrahydrothiopyranyl)eth-1-ene-2-carboxylate
tert.-butyl 1-(4-tetrahydrothiopyranyl)eth-1-ene-2-carboxylate
tert.-phenyl 1-(4-tetrahydrothiopyranyl)eth-1-ene-2-carboxylate The compounds I which can be prepared by the process according to the invention and the novel compounds I' are suitable as intermediates for active compounds in crop protection (DE-A-3,437,238, DE-A-3,536,117 and DE-A-3,601,066).

EXAMPLES

Example 1

Preparation of 1-(4-tetrahydropyranyl)but-1-en-3-one 5.0 g of magnesium were introduced into 100 ml of anhydrous tetrahydrofuran. 25 g of 4-chlorotetrahydropyran were added dropwise under reflux under a nitrogen atmosphere, and the mixture was refluxed for 2 hours. A solution of 23.5 g of 1-(dimethylamino)but-1-en-3-one in 20 ml of anhydrous tetrahydrofuran was subsequently added dropwise to the reaction mixture, cooled to from 0° to 5° C., at a rate such that the internal temperature did not exceed 50° C., and the mixture was stirred at room temperature for a further 2 hours. For work-up, the reaction mixture was poured into a mixture of ice and dilute HCl, and extracted 3 times with 200 ml of chloroform, and the extracts were washed with saturated sodium chloride solution and dried over $MgSO_4$. Removal of the solvent gave 24.0 g (75%) of 1-(4-tetrahydropyranyl)but-1-en-3-one having a boiling point of 117° C./10 mmHg.

Examples 2 to 4

The examples listed below were carried out in a manner similar to that of Example 1. The results are shown in the table below.

| Example No. | Solvent | $R^3$<br>$\diagdown$<br>$N-$<br>$\diagup$<br>$R^4$ | Yield |
|---|---|---|---|
| 2 | Diethyl ether | $CH_3$<br>$\diagdown$<br>$N-$<br>$\diagup$<br>$CH_3$ | 62 |
| 3 | Tetrahydrofuran | $C_2H_5$<br>$\diagdown$<br>$N-$<br>$\diagup$<br>$C_2H_5$ | 63 |
| 4 | Tetrahydrofuran | $CH_3$<br>$\diagdown$<br>$N-$<br>$\diagup$<br>$C_6H_5$ | 45 |
| 5 | Tetrahydrofuran | 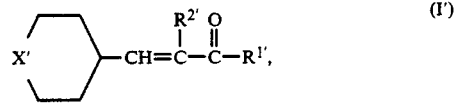 | |
| 6 | Tetrahydrofuran | 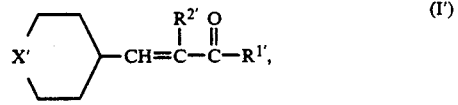 | |

Example 7

Preparation of 1-(4-tetrahydropyranyl)but-1-en-3-one 10.8 g (400 mmol) of Mg turnings are introduced into 30 ml of tetrahydrofuran containing a catalytic amount of iodine, and 5 ml of 4-chlorotetrahydropyran are added. The mixture is warmed to 50° C., and 45.2 g (375 mmol) of 4-chlorotetrahydropyran, dissolved in 120 ml of tetrahydrofuran, are added dropwise at such a rate that the internal temperature does not exceed 70° C. The mixture is stirred for a further 1 hour and subsequently cooled to room temperature. 42.4 g (375 mmol) of 1-(dimethylamino)but-1-en-3-one are added dropwise to the stirred mixture at such a rate that the reaction temperature does not exceed 30° C. The mixture is subsequently stirred for a further 2 hours and hydrolyzed, and the pH of the solution is adjusted to exactly 7. The phases are separated, and the aqueous phase is extracted several times with 200 ml of ethyl acetate or methyl tert.-butyl ether, dried and subjected to fractional distillation, to give 42.0 g (75%) of 1-(4-tetrahydropyranyl)but-1-en-3-one of boiling point 93° to 95° C./5 mmHg.

Example 8

Preparation of ethyl 1-(4-tetrahydropyranyl)eth-1-ene-2-carboxylate 9.6 g (400 mmol) of magnesium turnings are covered with tetrahydrofuran, about 2 ml of bromomethane are added, and the mixture is warmed to reflux. 38.45 g (300 mmol) of 4-chlorotetrahydropyran, dissolved in 100 ml of tetrahydrofuran, are added dropwise. The mixture is subsequently stirred for a further 30 minutes and cooled to 10° C., 42.9 g (300 mmol) of ethyl 1-(dimethylamino)eth-1-ene-2-carboxylate are added dropwise, and the mixture is stirred for a further 12 hours. Customary work-up gives 31.4 g (60%) of ethyl 1-(4-tetrahydropyranyl)eth-1-ene-2-carboxylate of boiling point 120° to 140° C./10 mmHg.

We claim:

1. A 1-(4-tetrahydropyranyl)- or 1-(4-tetrahydrothiopyranyl)prop-1-en-3-one of the formula I'

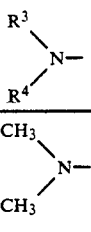

where the substituents have the following meanings:
$R^{1'}$ is hydrogen, $C_1$- to $C_{10}$-alkyl, $C_1$- to $C_{10}$-alkoxy or aryloxy,
$R^{2'}$ is hydrogen, $C_1$- to $C_4$-alkyl, and
$X'$ is oxygen or sulfur.

2. A compound of the formula I'

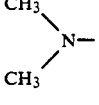

wherein $R^{1'}$ is methyl, $R^{2'}$ is hydrogen and $X'$ is oxygen.

* * * * *